United States Patent
Steiner (10) Patent No.: US 11,166,623 B2
(45) Date of Patent: Nov. 9, 2021

(54) FIELD STOP FLUORESCENT INDICATOR SYSTEM AND METHOD

(71) Applicant: ARTHREX, INC., Naples, FL (US)

(72) Inventor: Michael Steiner, Goleta, CA (US)

(73) Assignee: ARTHREX, INC., Naples, FL (US)

( * ) Notice: Subject to any disclaimer, the term of this patent is extended or adjusted under 35 U.S.C. 154(b) by 273 days.

(21) Appl. No.: 16/391,966

(22) Filed: Apr. 23, 2019

(65) Prior Publication Data

US 2020/0337525 A1    Oct. 29, 2020

(51) Int. Cl.
| | |
|---|---|
| *A61B 1/00* | (2006.01) |
| *A61B 1/04* | (2006.01) |
| *A61B 1/045* | (2006.01) |
| *A61B 1/06* | (2006.01) |
| *A61B 1/07* | (2006.01) |

(52) U.S. Cl.
CPC ...... *A61B 1/00055* (2013.01); *A61B 1/00006* (2013.01); *A61B 1/00057* (2013.01); *A61B 1/00059* (2013.01); *A61B 1/043* (2013.01); *A61B 1/045* (2013.01); *A61B 1/0638* (2013.01); *A61B 1/0653* (2013.01); *A61B 1/07* (2013.01)

(58) Field of Classification Search
CPC ............ A61B 1/00057; A61B 1/00059; A61B 1/00055; A61B 1/00006; A61B 1/043; A61B 1/045; A61B 1/0638
See application file for complete search history.

(56) References Cited

U.S. PATENT DOCUMENTS

| | | | | |
|---|---|---|---|---|
| 4,983,019 A | * | 1/1991 | Ikuno | G02B 6/0006 600/181 |
| 5,001,556 A | * | 3/1991 | Nakamura | H04N 9/0455 348/70 |
| 5,507,287 A | * | 4/1996 | Palcic | A61B 1/00186 356/318 |
| 5,630,782 A | * | 5/1997 | Adair | A61B 1/00073 600/123 |

(Continued)

FOREIGN PATENT DOCUMENTS

| | | | | |
|---|---|---|---|---|
| JP | 2002065584 A | * | 3/2002 | ......... A61B 1/00057 |
| JP | 3962122 | | 8/2007 | |
| JP | 4538141 | | 9/2010 | |

OTHER PUBLICATIONS

"Aperture and field stops" by Course Wiki, Jul. 25, 2015, pp. 1-2.
International Search Report and Written Opinion, dated Jul. 8, 2020.

*Primary Examiner* — Alexandra L Newton
*Assistant Examiner* — Jae Woo
(74) *Attorney, Agent, or Firm* — Karish & Bjorgum, PC (57) ABSTRACT

An endoscope for imaging a fluorescent agent in a patient, the endoscope having a first optical channel communicating light from a first light source and a second light source, the first light source having an excitation wavelength and the second light source having a wavelength different than the wavelength of the first light source; a field stop having a fluorescent indicator; and a second optical channel in optical communication with the first light source and in optical communication with the fluorescent indicator on the field stop. When light from the first light source illuminates the fluorescent indicator on the field stop, the fluorescent indicator is detectable. Image processing components used with the endoscope can identify the fluorescent indicator, or lack thereof, and transmit information to a user.

15 Claims, 5 Drawing Sheets

(56) References Cited

U.S. PATENT DOCUMENTS

| | | | | |
|---|---|---|---|---|
| 5,713,364 | A * | 2/1998 | DeBaryshe | A61B 1/00059 |
| | | | | 250/461.2 |
| 5,749,830 | A * | 5/1998 | Kaneko | A61B 1/00082 |
| | | | | 348/E5.038 |
| 6,293,911 | B1 * | 9/2001 | Imaizumi | A61B 1/00009 |
| | | | | 600/160 |
| 6,510,338 | B1 * | 1/2003 | Irion | A61B 1/00186 |
| | | | | 600/160 |
| 6,582,363 | B2 * | 6/2003 | Adachi | A61B 1/00009 |
| | | | | 600/160 |
| 6,631,287 | B2 | 10/2003 | Newman et al. | |
| 6,663,561 | B2 * | 12/2003 | Sugimoto | A61B 1/0638 |
| | | | | 348/E5.038 |
| 2002/0022763 | A1 * | 2/2002 | Sano | A61B 1/00108 |
| | | | | 600/109 |
| 2004/0263643 | A1 * | 12/2004 | Imaizumi | A61B 1/00009 |
| | | | | 348/222.1 |
| 2005/0261551 | A1 * | 11/2005 | Couvillon, Jr. | A61B 1/00105 |
| | | | | 600/118 |
| 2006/0155166 | A1 * | 7/2006 | Takahashi | A61B 1/045 |
| | | | | 600/109 |
| 2008/0306337 | A1 * | 12/2008 | Livingston | A61B 5/0075 |
| | | | | 600/109 |
| 2009/0192390 | A1 * | 7/2009 | Berguer | A61B 5/0071 |
| | | | | 600/476 |
| 2011/0205651 | A1 * | 8/2011 | Yamano | H04N 5/332 |
| | | | | 359/894 |
| 2012/0059222 | A1 * | 3/2012 | Yoshida | A61B 1/00091 |
| | | | | 600/157 |
| 2014/0046131 | A1 * | 2/2014 | Morita | H04N 5/232 |
| | | | | 600/109 |
| 2019/0069760 | A1 * | 3/2019 | Hygelund | A61B 1/00105 |

* cited by examiner

FIELD STOP FLUORESCENT INDICATOR SYSTEM AND METHOD

BACKGROUND

Endoscopic/arthroscopic imaging systems provide a surgeon with a view of an area of the body being worked on without the necessity of fully opening up the area, thereby allowing for less invasive surgical procedures. In fluorescence based imaging systems, a fluorescent visualization agent, such as indocyanine green (ICG), is administered to the patient during the imaging procedure and near-infrared (NIR) imaging is used to obtain a fluorescence based image. Fluorescence based imaging systems have specialized light sources and specially adapted camera systems to expand the spectrum of diagnostic options and enable the perfusion evaluation of organs and tissues. During a fluorescence based imaging procedure, the imaging system requires specialized instruments, depending on the fluorescent agent used, as different fluorescent agents have different emission/excitation profiles. The scope, camera, emission source, excitation source, light guide, firmware and software all have to work in unison to display and/or optimize the fluorescence based image. If the system setup is incorrect, for example an incorrect scope or an incorrect light guide is attached, the procedure can be delayed, leading to poorer patient outcomes. If the software is not properly functioning, or, the excitation source (e.g., a laser excitation source) is not functioning, there may also be a delay in the procedure. Troubleshooting for an error during the procedure causes an undesirable delay as both user error and/or a system fault may be the root cause of the failure and sorting out the error may be time consuming. Current fluorescence based imaging systems are subject to error and procedure delay due to incorrect software and/or system setup for fluorescence based imaging selected by the physician. Therefore, there is a need for an improved system which allows the user/physician to identify the endoscope and determine the system parameters for the surgical imaging system.

SUMMARY

According to the present invention, an endoscope and endoscopic imaging system and method used in surgical fluorescent imaging systems is provided, particularly endoscopic and arthroscopic surgical procedures. More particularly, an encoding system for surgical devices that requires specialized instruments for fluorescence based visualization, such as ICG based visualization or other agents with specialized emission/excitation profiles requiring specialized instrumentation and/or wavelength emission calibration is provided.

According to one embodiment, an endoscope for imaging a fluorescent agent in a patient is provided. The endoscope comprises a first optical channel communicating light from a first light source and a second light source, the first light source having an excitation wavelength and the second light source having a wavelength different than the first wavelength. The endoscope also has a field stop with a fluorescent indicator. The endo scope also has a second optical channel in optical communication with the first light source and in optical communication with the fluorescent indicator on the field stop. The field stop and fluorescent indicator are in optical communication with the second optical channel and the first light source to "back-light" the fluorescent indicator on the field stop. When light from the first light source illuminates the fluorescent indicator on the field stop, the fluorescent indicator on the field stop is identifiable (i.e., detectable) to a user of the endoscope. The fluorescent indicator may be indocyanine green and the first light source may have an excitation wavelength in the near infrared.

According to another embodiment, an endoscopic imaging system for imaging a fluorescent agent in a patient is provided. The system comprises an endoscope having a first optical channel for communicating light from a first light source and a second light source. The first light source has an excitation wavelength and the second light source has a wavelength different than the first light source. A field stop having a fluorescent indicator is positioned in optical communication with a second optical channel in optical communication with the first light source. A camera head, coupleable to the endoscope, is configured to generate image data comprising image data from the field stop. A camera control unit, which is coupleable to the camera head, is configured to (i) receive image data from the camera head, and (ii) detect a presence of the fluorescent indicator, and transmit an error message to a user if the fluorescent indicator is not detected. In some embodiments, the system also has a memory coupled to the camera control unit where the camera control unit obtains endoscope usage information from the memory. In other embodiments, the system also has a display device coupled to the camera control unit where the display device displays information about the endoscope as identified by the fluorescent indicator on the field stop.

According to another embodiment, a method of communicating endoscope information from an endoscope having a field stop to user in an endoscopic imaging system is provided. The method comprises the steps of first, providing an endoscope having a field stop with a fluorescent indicator positioned on the field stop. A camera head is coupled to the endoscope. The camera head generates image data comprising the fluorescent indicator positioned on the field stop. Image data is transmitted from the camera head to a camera control unit. The image data is analyzed to detect the fluorescent indicator to identify the endoscope coupled to the camera head. In another embodiment, the system validates whether the endoscope is appropriate for use with one or more of a first light source, a second light source, and the camera head. In another embodiment, the system transmits to a user whether the endoscope is appropriate for use with one or more of the first light source, the second light source, and the camera head. The system may also modify one or more parameters of the endoscope or system based upon the identified endoscope and/or calibrate fluorescence intensity in the endoscopic imaging system based on the detecting fluorescent indicator positioned on the field stop.

These and other features of the present invention are described below.

BRIEF DESCRIPTION OF THE DRAWINGS

The features, aspects and advantages of the present invention will become better understood with regard to the following description, appended claims and accompanying figures wherein:

DETAILED DESCRIPTION

In the following description of the preferred embodiments, reference is made to the accompanying drawings which show by way of illustration specific embodiments in which the invention may be practiced. Wherever possible, the same reference numbers will be used throughout the drawings to refer to the same or like parts. It is to be understood that other embodiments may be utilized and structural and functional changes may be made without departing from the scope of the present invention.

According to the present invention, an endoscope, endoscopic imaging system, and method are provided where a fluorescent indicator is embedded in the field stop of the endoscope. The fluorescent indicator is back-lit by a light source from a secondary channel. Accordingly, the wavelength emission embedded in the endoscope identifies the endoscope and alternately allows for fluorescent intensity calibration in the system. With the fluorescent wavelength emission of the system embedded in the scope, the visualization system has a reference point from which the system can be automatically calibrated and live scene fluorescence intensity can be measured without user input. Since this calibration takes place at the input of the visualization system, variance in light guide, laser source, camera optics can all be calibrated for optimum performance. The endoscope and fluorescent imaging system of the present invention, having features that can indicate correct system configuration to a user, minimizes the risk of incorrect system configuration and improves patient outcome. Further, automated calibration of the fluorescence intensity measurement of the system improves the imaging quality and system performance.

Referring now to FIG. 1 and FIGS. 2A-2D, an illustration of an endoscope 10 having a field stop 100 with a fluorescent indicator 102 positioned in the field stop 100, according to one embodiment of the invention, is shown. The fluorescent indicator 102 on the field stop is detectable upon illumination (i.e., excitation) by a light source of the appropriate wavelength, and subsequent image capture and processing of the fluorescent indicator, which is then used to identify the endoscope 102. Alternately, if the system setup is incorrect, for example an incorrect scope, light guide, or laser source, the system can notify a user.

Figure 1:
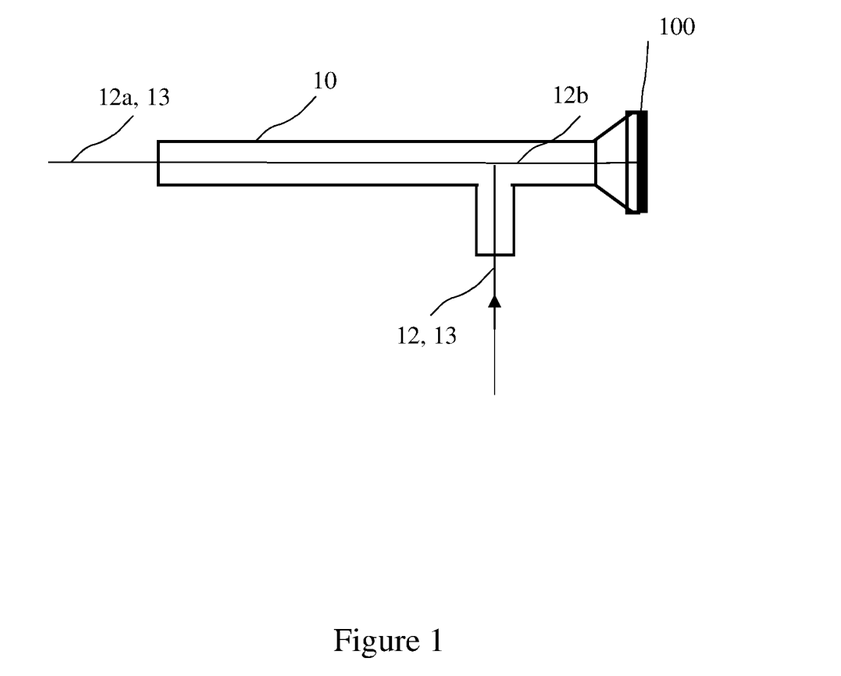
FIG. 1 is an illustration of an endoscope having a fluorescent indicator embedded in the field stop according to one embodiment of the present invention.
Figure 2A:
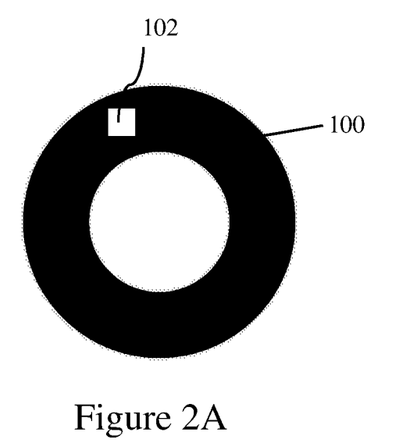
FIGS. 2A, 2B, 2C and 2D illustrate various embodiments of field stops having a fluorescent indicator usable with the endoscope shown in FIG. 1, according to other embodiments of the present invention
Figure 2B:
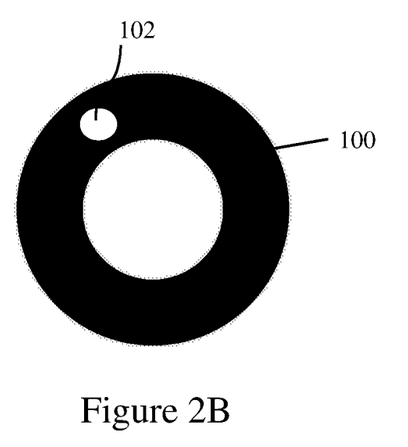
Figure 2C:
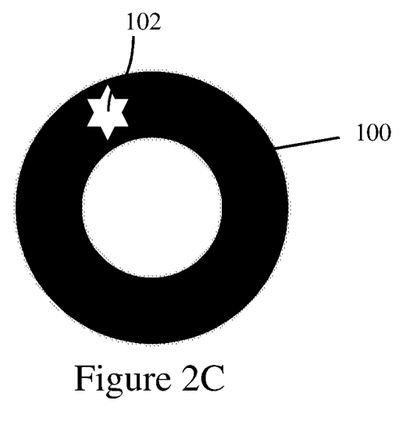
Figure 2D:
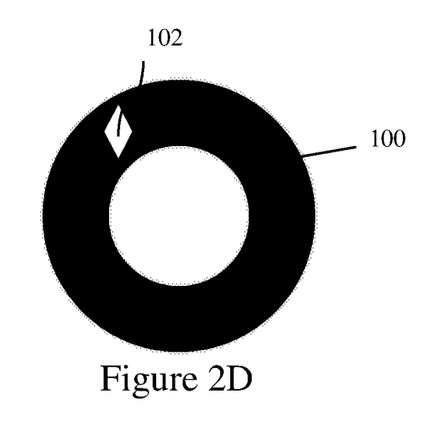

As shown in FIG. 1, the endoscope 10 comprises a first optical channel having a first light source 12 and a second light source 13, the first light source 12 has a wavelength in the near-infrared and the second light source has a wavelength different than the wavelength of the first light source. The field stop 100 is positioned on an end of the endoscope 10. The first light source 12 is split into two channels, the first light source in the first optical channel 12a, and the first light source in the second optical channel 12b. Light from the first light source is communicated through the second optical channel, 12b to the fluorescent indicator 102 on the field stop 100.

Preferably, the first light source 12 is at a first wavelength in the near-infrared, NIR, and is configured to image a fluorescent agent administered to a patient from the light source 12a in the first optical channel, such as internal organs and blood perfusion therein. The light source 12, is also configured to excite the fluorescent indicator 102 through the second optical channel.

The second light source 13, at a second wavelength, may be a light source within the visible range, and is configured to image a surface of the patient. Preferably, the first light source 12 and the second light source 13 are configured to image the patient through the first optical channel simultaneously.

Referring again to FIG. 2A-2D, different embodiments of the field stop 100 are shown. The field stop 100 on the endoscope 10 controls unwanted stray light. The field stop 100 produces a round aperture in the field of view. The field stop 100 may be a small black metal mask with the fluorescent indicator 102 placed at a specific location in the optical path of the second channel on the inside of the endoscope 10.

The fluorescent indicator 102 on the field stop may be of a variety of shapes, for example a dot (circle or oval), square, star, diamond, or slot, for example, and the shape may be used for further identification of the endo scope 10. The fluorescent indicator 102 is back-lit by the excitation light 12a, from, for example, a fiber optic channel, when the user enters the fluorescence mode of the system, and image processing checks the field stop for emission of the fluorescent indicator. For example, a green dot in the case of indocyanine green (ICG) indicates a correct configuration. If the system does identify the presence of the fluorescent indicator, by color and/or shape, the endoscope configuration is incorrect and the system can provide further information to the user for troubleshooting.

Although the fluorescent agent indocyananine green (ICG) is referred to herein as a preferred embodiment, other fluorescent agents are envisioned as within the scope of the invention, as will be understood by those of skill in the art, such as other rhodamine and cyanine based fluorescent agents, or fluorescent nanoparticles. Preferred fluorescent agents are approved for medical use and administrable to a patient to endoscopically observe blood perfusion. Additionally, although near-infrared has been referred to herein as a preferred embodiment of an excitation light, other wavelengths of excitation light, such as ultraviolet, are envisioned as within the scope of the invention depending on the excitation wavelength of the selected fluorescent agent, as will be understood by those of skill in the art.

In addition, the fluorescent indicator 102 is not limited to the same fluorescent agent used in the patient procedure. Other, 'back-lit' fluorescent materials can be used to emit the desired wavelength in the field stop. In some embodiments, the fluorescent indicator 102 on the field stop 100 is the same fluorescent compound as the fluorescent agent imaged in the patient. In an exemplary embodiment, ICG is administered to a patient for imaging the patient and the fluorescent indicator 102 on the field stop 100 is also ICG. In other embodiments, the fluorescent indicator 102 on the field stop 100 is a different fluorescent compound than the fluorescent agent imaged in the patient but the fluorescent compound on the field stop 102 has an excitation and emission spectrum which overlap with the fluorescent agent imaged in the patient. In this exemplary embodiment, IGC is administered to a patient for imaging, but the fluorescent indicator 102 positioned on the field stop 100 is a second fluorescent compound which has an emission/excitation profile similar (overlapping) to that of ICG for identification and calibration, e.g., a second fluorescent compound having an excitation maximum at 788 nm and an emission maximum at 813 nm, ±8 nm. In some embodiments, the fluorescent indicator 102 is a second fluorescent compound which is photo stable and heat stable and not subject to degradation, or limited degradation, over time. The fluorescent indicator 102 is embedded in the field stop 100 and may comprise additional compounds to stabilize the fluorescent indicator 102 from degradation from heat, time, and/or photo degradation. Additionally, the fluorescent indicator 102 may be encapsulated within the field stop 100 in a material which allows for optical communication with the light source 12a and imaging by the system 200, but that does not interfere with the fluorescent emission of the fluorescent indicator 102 and subsequent imaging and detection of the field stop 100 and fluorescent indicator 102.

Figure 3:
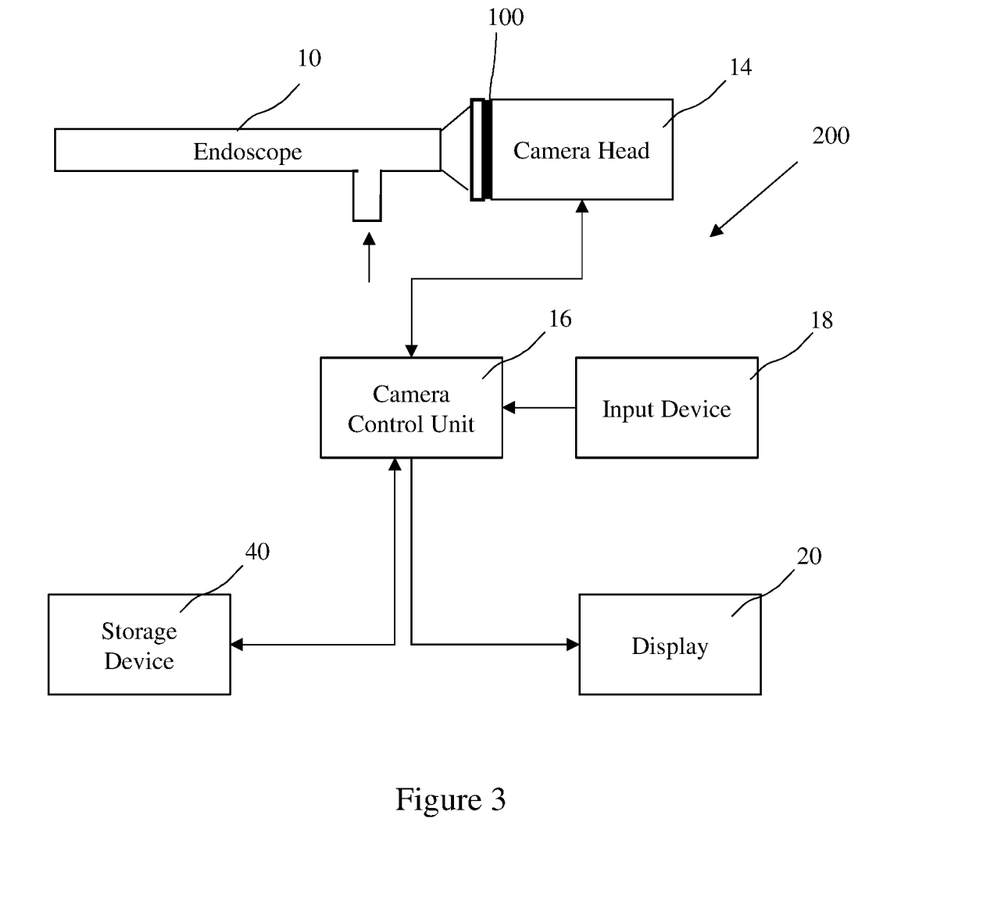
FIG. 3 is a schematic diagram of an endoscopic imaging system usable with the endoscope of FIG. 1.
Figure 4:
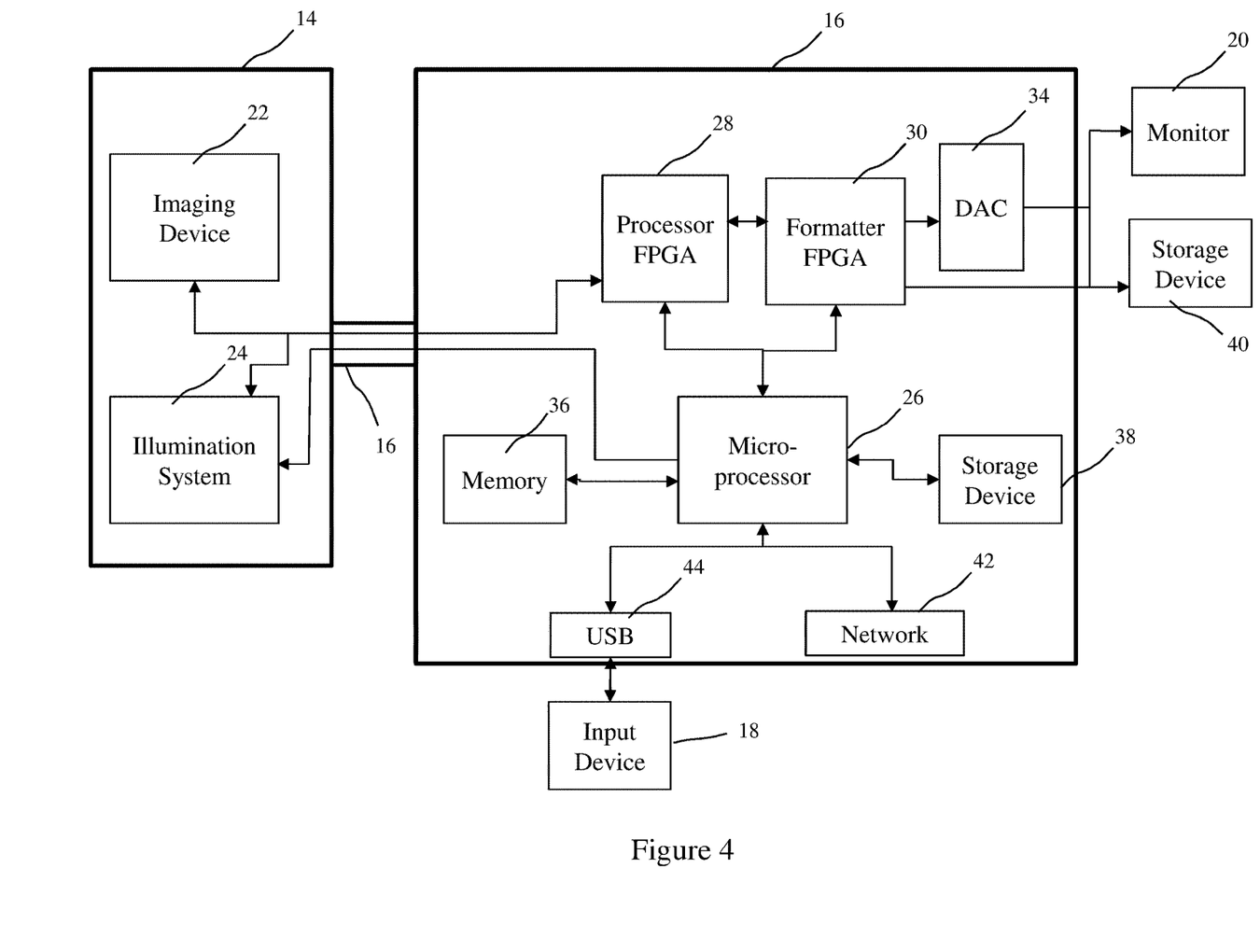
FIG. 4 is a schematic diagram of a camera control unit and camera head usable with the system of FIG. 3.

Referring now to FIGS. 3 and 4, an endoscopic imaging system 200 for imaging a fluorescent agent in a patient is shown. The endoscope 10 comprises a field stop 100 having a fluorescent indicator 102, as described herein, and first and second light sources (12, 13). As shown in FIG. 3, the endoscopic imaging system 200 has at least one endoscope 10 connectable to a camera head 14. The camera head 14 is connectable to a camera control unit 16 ("CCU"). The camera head 14 and camera control unit 16 may be connected via wire or wirelessly. The camera control unit 16 is also connectable to at least one input device 18 such as a mouse, keyboard, touchpad, or touchscreen monitor. Additionally, the camera control unit 16 is connectable to a display 20. The camera head 14 generates image data including image data from the field stop. The camera control unit 16 is configured to receive image data from the camera head 14 and identify the endoscope 10 from the fluorescent indicator 102, or transmit an error message to a user if a fluorescent indicator 102 is not identified or identified as incompatible with the system 200.

According to the invention, the camera control unit 16 receives image data from the camera head 14 including an image of at least a portion of the field stop 10. The fluorescent indicator 102 may be identified by an image processing algorithm that scans the field stop image data received from the camera head 14 to identify the fluorescent indicator 102 on the field stop 10 using the contrast of the pixels in the field stop image. In some embodiments, in addition to the identification of the fluorescent indicator 102 on the field stop image, the approximate known location and/or shape of the fluorescent indicator 102 may be used to identify the field stop 100, which is then correlated by the processing algorithm with information about the endoscope 10.

In some embodiments, the pixels in the field stop 100 are extracted from the image data. The pixels are then analyzed for the presence of the fluorescent indicator 102. Optionally, the expected location of the fluorescent indicator 102 can be determined from other features of the stop mask, such as a visualization marker in the edge of the field stop 100.

According to another embodiment of the invention, once the endoscope 10 is identified from the fluorescent indicator 102 on the field stop 100, the system 200 automatically adjusts operational settings of the camera head 14 and/or camera control unit 16 to calibrate or optimize the settings of the system 200 in accordance with the endoscope 10 coupled to the camera head 14. In an exemplary embodiment, upon engagement of the system by the user, the system 200 receives information on the fluorescent indicator 102, for example, the system detects an ICG emissions signal and the system 200 automatically calibrates the live scene ICG intensity of the camera 14. The system 200 may also automatically calibrate to compensate for a variance in a light guide, light source, and/or camera optics for optimum performance of the system.

As shown in FIG. 3, the camera head 14 has an imaging device 22 which may include NTSC/PAL, single chip, three chip, standard definition, high definition, ultra high definition, CCD and CMOS devices. The camera head may also have an illumination system 24. The camera head 12 may also have memory for storing camera data, camera control unit processing data or other information. The camera head 12 may also have a user input means such as buttons to control aspects of image capture.

As shown in FIG. 4, the camera control unit 16 contains a microprocessor 26 for interfacing with user input devices 18, a signal processing circuit 28, a signal formatting circuit 30, digital to analog converters 34 and memory 36. The camera control unit 16 runs program applications providing for a variety of capabilities. For example, the camera control unit 16 may provide for a live feed of the image generated by the camera head 14 to be displayed through the display 20. Additionally, the camera control unit 16 may provide image capture functionality allowing for images generated by the camera head 14 to be saved to a storage device, such as an internal storage device 38 or a storage device 40 external to the camera control unit. The captured images may be annotated and/or edited and displayed through the display 20.

According to another embodiment, the camera control unit 16 also has at least one network interface 42 which may be a wired interface such as Ethernet, or a wireless network connection that allows for the camera control unit to access a network. Optionally, the network interface 42 allows the camera control unit 16 to access the Internet and servers for storing and processing information. According to another embodiment, external storage device 40 may be incorporated into the system 200. For example, a flash memory storage device or a hard disk storage device may be incorporated into the system 200 and may be connected to the camera control unit 14 through a USB connection 44 or firewire connection (not shown). In another embodiment, a program application for the camera control unit, or data relevant to a particular patient, surgeon or endoscope, is stored on the external storage device 40 and may be used to quickly configure the camera control unit for future sessions. Preferably, the camera control unit 16 can save images and video in different formats and to different places (e.g. internal memory, an external memory, or to a remote location over the Internet). Additionally, the external storage device 40 may be a server and may be connected to the camera control unit the network interface 42.

Figure 5:
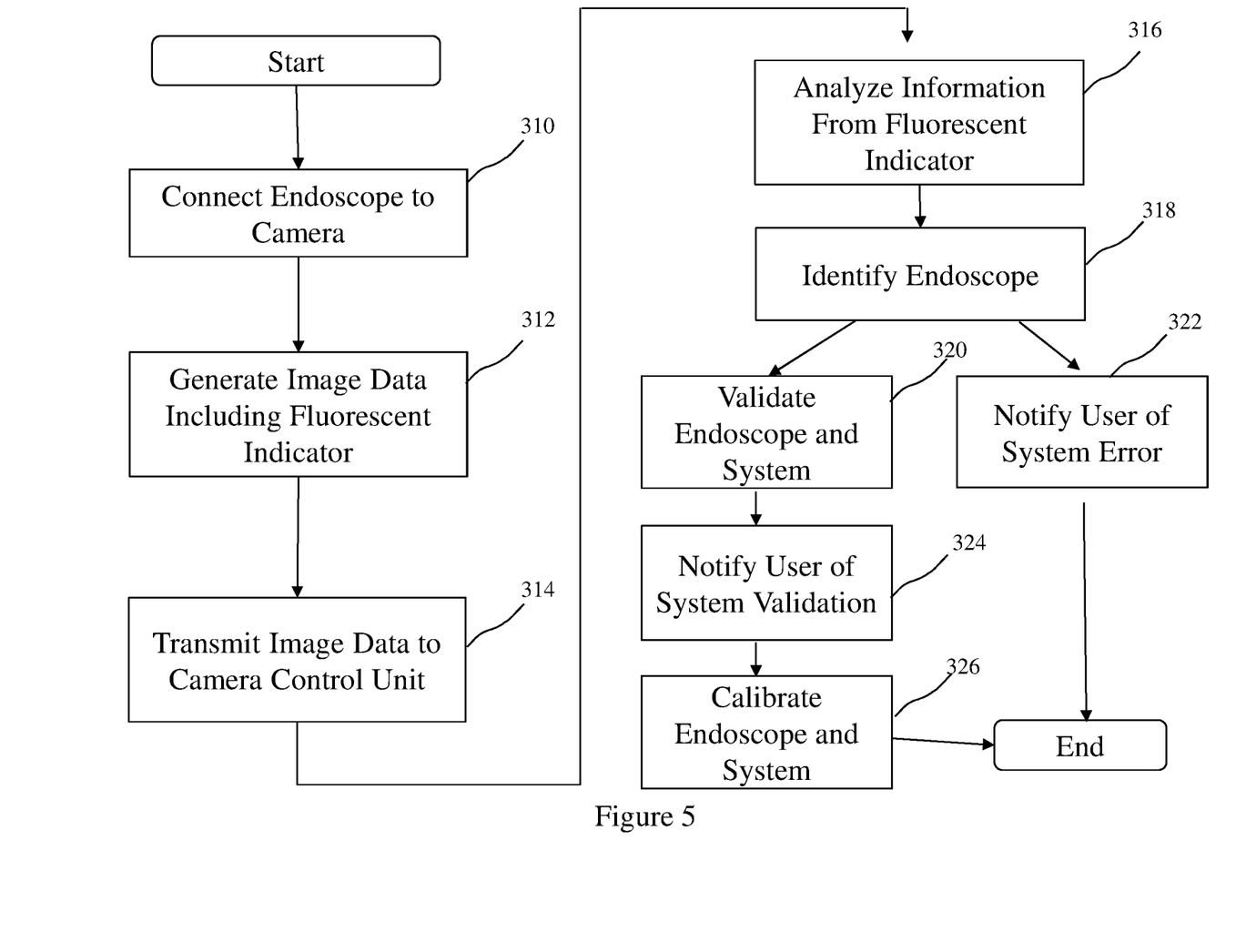
FIG. 5 is a block diagram showing an example of how endoscope information is obtained with the fluorescent indicator according to another embodiment of the present invention.

Referring now to FIG. 5, the present invention is also directed to a method of communicating endoscope information from an endoscope having a field stop to a user in an endoscopic imaging system. Initially, an endoscope having a field stop with a fluorescent indicator is coupled to a camera head, box 310. Next, image data is generated by the camera head comprising the fluorescent indicator positioned on the field stop, e.g., fluorescence data such as emission maxima, or emission spectra, or other variance in the pixilation of the field stop, box 312. This may be automatic or user initiated. The image data is then transmitted from the camera head to the camera control unit, box 314. The image data is then analyzed, box 316, to detect the fluorescent indicator to identify the endoscope coupled to the system, box 318. The system, including the endoscope, camera, and light sources, for example are then validated, box 320. Endoscope information can also be used to prevent the use of incompatible endoscopes. For example, if a scope is used that is not validated for use with a given camera system, the camera control unit 16 may cause a warning to be displayed to a user on the display 20. Endoscope information can also be used to identify whether the system setup is incorrect, for example an incorrect scope or light guide, an error message or indication of system malfunction is communicated to the user, box 322. Alternatively, if the system correctly validates, box 320, the system indicates to the user the system validation, box 324. The system validation may be variety or combination of indicators, such as a display screen communicated to the user, or a light system, for example, indicating system a correct set-up or system error. The system can indicate an overall error or isolate an error in one or more components of the system such as the first light source, the second light source, and/or the camera head.

Once endoscope information is obtained, the endoscope information can be used to optimize and calibrate one or more parameters of the endoscope or the system, box 326. For example, reference image processing, light settings, or display settings in a memory in the camera control unit or in a memory accessible by the camera control unit can be used to optimize and calibrate the system. The image processing, light settings, or display settings may be automatically implemented by the camera control unit. Also, for example, the image for a particular endoscope may be automatically magnified to a predetermined magnification. Also, for example, the operational settings of the camera head may be automatically adjusted for the specific endoscope. Also, for example, optimal light source settings, such as fluorescence intensity, may be automatically selected for the particular endoscope.

Additionally, the camera system can record and present usage statistics on which endoscopes are used, with which surgeries, and for how long. This data may be stored in a storage accessible to different camera control units so that the data may be updated when a particular endoscope is used in different locations with different camera heads and camera control units. This data can help surgeons keep records of which endoscopes were used in each procedure. Reliability of endoscopes can be more accurately tracked. Manufacturing, sales, and design may benefit from the data to make the most often used products, rather than relying on sales history.

Endoscope usage information is advantageous because usage time may affect the reliability and health of an endoscope. Once an endoscope is identified, target calibration can be used to gauge the health of the endoscope. For example, optimal light and exposure settings for a given type of endoscope may be compared with light and exposure settings used with the actual endoscope to determine whether the endoscope is functioning properly. The data may also be used to determine the health of different camera heads. For example, if the same endoscope is used with different camera heads and the usage requires very different light and exposure settings, then investigation of the camera heads may be warranted.

The present invention is advantageous, in that for the fluorescence imaging system to function properly, each of the components of the system, e.g., the endoscope, camera, excitation source, light guide, firmware and software all have to work in unison to display a useable fluorescence based image, e.g., an ICG image. The present invention identifies the endoscope based on fluorescence information encoded in the field stop and notifies the user of an incorrect set-up before a delay in a patient procedure. Identifying user error and/or system fault prior to a patient procedure greatly improves user experience and patient outcome. Another advantage of the present invention is that the intensity of wavelength emission embedded in the endoscope can be controlled and can allow for imaging system fluorescence intensity calibration, e.g., ICG or other fluorescent agent intensity calibration. As the fluorescence wavelength emission is embedded in the endoscope, the visualization system has a reference point from which the system can be automatically calibrated and live scene fluorescence intensity can be measured without user input. Since the calibration takes place at the input of the visualization system, variance in light guide, laser source, and/or camera optics can all be calibrated for optimum performance.

There is disclosed in the above description and the drawings, a surgical imaging system and method for processing surgical images that fully and effectively overcomes the disadvantages associated with the prior art. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. An endoscope for imaging a fluorescent agent in a patient, the endoscope comprising:
   a first optical channel communicating light from a first light source and a second light source, the first light source having an excitation wavelength and the second light source having a wavelength different than the wavelength of the first light source;
   a field stop having a fluorescent indicator; and
   a second optical channel in optical communication with the first light source and in optical communication with the fluorescent indicator on the field stop,
   wherein, when light from the first light source illuminates the fluorescent indicator on the field stop, the fluorescent indicator is detectable.

2. The endoscope according to claim 1 wherein the fluorescent indicator on the field stop comprises a dot.

3. The endoscope according to claim 1 wherein the fluorescent indicator on the field stop is the same fluorescent agent as the fluorescent agent imaged in the patient.

4. The endoscope according to claim 1 wherein the fluorescent indicator on the field stop is a different fluorescent compound than the fluorescent agent imaged in the patient but having an excitation and emission spectrum which overlap with the fluorescent agent imaged in the patient.

5. The endoscope according to claim 1 wherein the fluorescent indicator on the field stop is indocyananine green and wherein the first light source has an excitation wavelength in the near infrared.

6. The endoscope according to claim 1 wherein the fluorescent indicator on the field stop is a fluorescent compound having an excitation and emission spectrum which overlap with indocyanine green.

7. An endoscopic imaging system for imaging a fluorescent agent in a patient, the system comprising:
   An endoscope comprising:
   a first optical channel communicating light from a first light source and a second light source, the first light source having an excitation wavelength and the second light source having a wavelength different than the wavelength of the first light source, a field stop having a fluorescent indicator, and a second optical channel in optical communication with the first light source and in optical communication with the fluorescent indicator on the field stop;

a camera head coupleable to the endoscope, the camera head being configured to generate image data from the field stop;

a camera control unit coupleable to the camera head and configured to:

receive image data from the camera head;

detect a presence of the fluorescent indicator; and transmit an error message to a user if the fluorescent indicator is not detected.

8. The endoscopic imaging system according to claim 7 wherein the camera control unit automatically adjusts operational settings of the camera head in accordance with the endoscope coupled to the camera head, as identified by the fluorescent indicator on the field stop.

9. The endoscopic imaging system according to claim 7 wherein the camera control unit automatically adjusts operational settings of the camera control unit in accordance with the endoscope coupled to the camera head, as identified by the fluorescent indicator on the field stop.

10. The endoscopic imaging system according to claim 7 wherein the camera control unit automatically adjusts one or more of variance in the first or second light source, fluorescence intensity, and camera optics.

11. The endoscopic imaging system according to claim 7 wherein light at the first wavelength is configured to image a fluorescent agent administered to a patient and provide information related to the fluorescent agent in the patient to the camera control unit, and light at the second wavelength is configured to image a surface of the patient.

12. The endoscopic imaging system according to claim 7 wherein light from the first light source has an excitation wavelength in the near infrared and is configured to image an indocyanine green based fluorescent agent administered to patient and provide information related to the indocyanine green based fluorescent agent in the patient to the camera control unit, and light at the second wavelength is configured to image a surface of the patient.

13. The endoscopic imaging system according to claim 12 wherein the second light source emits light at a wavelength within the visible range.

14. The endoscopic imaging system according to claim 7 further comprising a memory coupled to the camera control unit and wherein the camera control unit obtains endoscope usage information from the memory.

15. The endoscopic imaging system according to claim 7 further comprising a display device coupled to the camera control unit, wherein the display device displays information about the endoscope as identified by the fluorescent indicator on the field stop.

* * * * *